United States Patent
Kato et al.

(10) Patent No.: US 7,763,448 B2
(45) Date of Patent: Jul. 27, 2010

(54) POROUS BODY FORMED OF SERICIN

(75) Inventors: Yoichi Kato, Fukui (JP); Kazuhisa Tsujimoto, Fukui (JP); Hideyuki Yamada, Fukui (JP)

(73) Assignee: Seiren Co., Ltd., Fukui (JP)

( * ) Notice: Subject to any disclaimer, the term of this patent is extended or adjusted under 35 U.S.C. 154(b) by 710 days.

(21) Appl. No.: 10/593,608

(22) PCT Filed: Mar. 17, 2005

(86) PCT No.: PCT/JP2005/005460

§ 371 (c)(1),
(2), (4) Date: Sep. 21, 2006

(87) PCT Pub. No.: WO2005/092960

PCT Pub. Date: Oct. 6, 2005

(65) Prior Publication Data

US 2007/0197701 A1    Aug. 23, 2007

(30) Foreign Application Priority Data

Mar. 25, 2004 (JP) .............................. 2004-089064

(51) Int. Cl.
*C12N 11/02* (2006.01)
*C07K 17/02* (2006.01)
(52) U.S. Cl. .................... 435/177; 530/353; 530/812
(58) Field of Classification Search .................... None
See application file for complete search history.

(56) References Cited

U.S. PATENT DOCUMENTS

| 6,365,149 B2 * | 4/2002 | Vyakarnam et al. ........ 424/93.1 |
| 6,815,427 B2 * | 11/2004 | Tsubouchi et al. ............. 514/21 |
| 7,115,388 B2 * | 10/2006 | Tsubouchi .................. 435/68.1 |

FOREIGN PATENT DOCUMENTS

| JP | 1-254621 | 10/1989 |
| JP | 2000-38514 | 2/2000 |
| JP | 2000-106868 | 4/2000 |
| JP | 2003-214766 | 7/2003 |
| JP | 2004-2521 | 1/2004 |

* cited by examiner

*Primary Examiner*—David M Naff
(74) *Attorney, Agent, or Firm*—Dilworth & Barrese, LLP.

(57) ABSTRACT

The present invention provides a porous body high in safety against environment and living bodies and having a strength high enough to withstand practical use, said porous body comprising, as a skeleton constituent thereof, sericin with an average molecular weight of 30000 to 400000, and having a recovery rate of 10 to 100% after 50% compression.

8 Claims, 1 Drawing Sheet

POROUS BODY FORMED OF SERICIN

FIELD OF ART

The present invention relates to a porous body having biocompatibility and a method for producing the same. More particularly, the present invention is concerned with a porous body of sericin high in safety against environment and living bodies and having a strength high enough to withstand practical use, as well as a method for producing the porous body.

BACKGROUND ART

Cocoon thread discharged from a silkworm is constituted by two kinds of proteins which are a highly crystalline fibroin and a non-crystalline sericin. The sericin is present in a conglutinated state so as to surround two fibroins. A fiber after removal of sericin by scouring and containing fibroin as a main component is what is called silk thread. Heretofore, sericin has been discarded to waste as being of no value.

Recently, however, it has turned out that sericin possesses such properties as moisture retaining property, anti-oxidation action, cell protecting action, and protein protecting action, and is superior in biocompatibility. With this finding, attempts to utilize sericin as such a functional material as medical or cosmetic material have come to be conducted actively.

For example, in JP 3(1991)-284337A there is described a crosslinked polymer separation membrane formed by crosslinking sericin with formaldehyde and a heat-reactive water-soluble urethane resin into a thin membrane. In JP 6 (1994)-80741A there is described a protein-containing synthetic polymer material formed by emulsion-polymerizing a protein such as sericin with acrylonitrile and a protein-containing synthetic polymer material formed by joining and crosslinking a protein such as sericin with a water-soluble epoxy compound and a crosslinking agent into a three-dimensional network structure. In JP 2001-106794A there is described a polymeric hydrous gel formed by crosslinking a blend of sericin and polyvinyl alcohol by a crosslinking agent into an insoluble state. In JP 2002-201363A there is described a composite resin consisting of sericin and a polyvinyl alcohol-based water-soluble resin and capable of being subjected to thermoforming in a melted state.

However, in all of the above conventional techniques, sericin is made difficult to dissolve or insoluble with use of a synthetic polymer or the properties of sericin are slightly imparted to a synthetic polymer. Safety against environment and living bodies is not satisfactory and a limit is encountered in using the respective products as functional materials, especially as medical materials.

On the other hand, for example in JP 11(1999)-228837A there is described a silk protein/collagen composite prepared by evaporating to dryness a mixed aqueous solution or dispersion of silk protein and collagen and allowing solidification to take place. In JP 2003-192807A is described a silk protein cast film formed by drying an aqueous solution of silk protein in an inert atmosphere condition. It is described therein that the silk protein is either sericin or fibroin.

Indeed these techniques appear to overcome the foregoing problem related to safety, but as to JP 11(1999)-228837A, many of collagens available on the market are derived from cowhide and there is the recent tendency to refraining the use thereof because problems, including the problem of bovine spongiform encephalopathy, are coming into question.

Further, in JP 11(1999)-228837A and JP 2003-192807A, a silk protein is substantially fibroin alone or a mixture of fibroin and sericin, and even if sericin alone is used as a silk protein, it has so far been impossible to obtain a composite or cast film having a strength high enough to withstand practical use.

Subjecting sericin to freeze-drying is also performed for the purpose of preparing a powder of sericin. However, there has not been conducted yet any attempt to use sericin alone as a skeleton constituent of a porous body and obtain a porous body having a structural stability high enough to withstand practical use.

OBJECT OF THE INVENTION

The present invention has been accomplished in view of the above-mentioned circumstances and it is an object of the invention to provide a porous body of sericin highly safe for the environment and living bodies, having a strength high enough to withstand practical use and employable suitably as a functional material, as well as a method for producing such a porous body.

SUMMARY OF THE INVENTION

The present invention firstly resides in a porous body comprising, as a skeleton constituent thereof, sericin with an average molecular weight of 30000 to 400000, and having a recovery rate of 10 to 100% after 50% compression.

Preferably, the porous body of the present invention has an average pore diameter of 0.1 to 5000 μm and a porosity of 70 to 99%.

The porous body of the present invention may contain a functional substance in an immobilized state if necessary.

The present invention secondly resides in a method for producing a porous body, the method comprising gelling an aqueous solution containing sericin with an average molecular weight of 30000 to 400000, thereafter freezing the resulting gels and then melting the frozen gels.

According to the present invention it is possible to provide a porous body having a strength high enough to withstand practical use basically from sericin alone without using any compound that is likely to exert a bad influence on the environment or living bodies. Besides, by incorporating a functional substance in the porous body it is possible to impart a novel functionality to the porous body and stabilize and immobilize the thus-incorporated functional substance physically. Moreover, it is possible to suppress deactivation of the functional substance which can occur due to stress such as freezing for example. The porous body provided by the present invention is employable suitably as a functional material such as a medical or cosmetic material, food material, or environment-compatible material. More concrete examples include reproduced medical engineering material, cell matrix, biosensor, bioreactor, moisture retaining material, temperature retaining material, microorganism immobilizing carrier, drug pasting sheet, and soil conditioner.

EMBODIMENTS OF THE INVENTION

Figure 1:
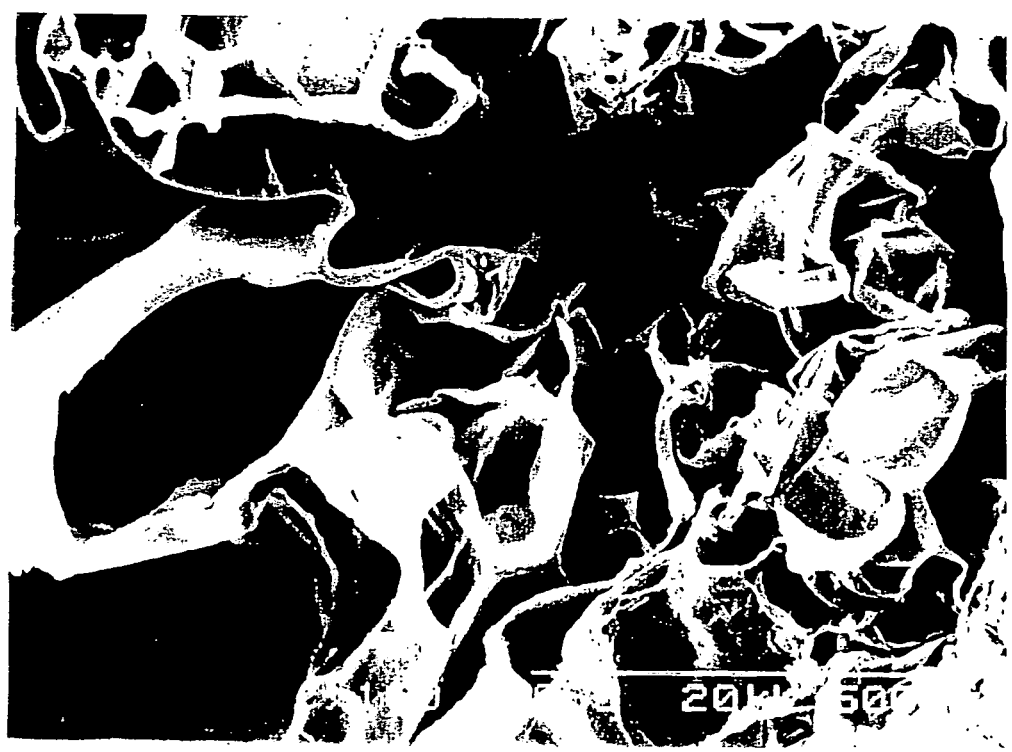
FIG. 1 is an electron micrograph from observation of the porous body through an electron microscope.

The present invention will be described in detail hereinafter.

The sericin which constitutes the porous body is required to have an average molecular weight of 30000 to 400000. If the average molecular weight is less than 30000, it is impossible to constitute a porous body of sericin having a practical strength. If the average molecular weight exceeds 400000, the sericin is difficult to dissolve in water and the operability thereof is poor. The average molecular weight is preferably 40000 to 200000, more preferably 60000 to 100000. The molecular weight or average molecular weight of sericin in the present invention is a value measured by sodium dodecyl sulfate—polyacrylamide gel electrophoresis (SDS-PAGE). It is preferable that sericin having a molecular weight of 30000 to 400000 occupies 70 to 100%, more preferably 95 to 100%, still more preferably 99 to 100%, of the sericin used in the present invention. The purity of sericin is preferably 90 to 100%, more preferably 95 to 100%, still more preferably 99 to 100%. The "purity" as referred to herein indicates the ratio of sericin to the content of solids contained in an aqueous solution of sericin obtained by separation and purification or the content of solids obtained by drying. The solids contains slight amounts of impurities such as cocoon- or silkworm-derived components such as proteins (e.g. fibroin), amino acids, sugar, lipid, nucleic acid and pigments, and salt.

The sericin used in the present invention may be one derived from a natural substance or an artificially synthesized one insofar as an average molecular weight thereof is in the range of 30000 to 400000. Thus, the sericin may be a chemically synthesized one or one obtained by genetic engineering means. In the present invention, however, the sericin is preferably one derived from a natural substance. Sericin derived from a natural substance is advantageous because it is highly safe for living bodies and it can be prepared relatively easily. The sericin as referred to herein includes not only the sericin protein itself but also a hydrolyzate of the said protein.

According to a preferred embodiment of the present invention there is used sericin extracted from cocoon threads discharged from silkworms or from raw silk with use of a solvent or sericin isolated physically. Sericin present within silk glands taken out from the interiors of silkworms is also employable. By the cocoon as referred to herein is meant a silkworm cocoon and by the raw silk as referred to herein is meant a cocoon thread obtained by delivery from a silkworm cocoon immersed in hot water.

The silkworm used in the present invention is not specially limited. Both a domestic silkworm raised and grown by a human and a wild silkworm which grows in the natural environment are employable. The cocoon may be in a state in which it contains a pupa, or in a state in which it has been partially cut out to take out the pupa, or in a pulverized state. The raw silk may be in a state in which it has been subjected reeling, or in a state in which it has been made into fabric for example by weaving or by knitting, or in a state in which it has been subjected to sewing, or in a pulverized state.

As examples of the extraction solvents used for obtaining sericin from the above materials there are mentioned water and hydrophilic solvents, including an aqueous solution of urea and aqueous alcohols. For example, sericin is dissolved out into water by boiling domestic cocoons with water in an amount of 10 to 30 times as large as the amount of the cocoons. At this time, where required, the sericin may be partially hydrolyzed by using electrolyzed water, acid, alkali, or enzyme. Further, the sericin may be treated under pressure. As noted earlier, the sericin used in the present invention is required to have an average molecular weight of 30000 to 400000. For efficient extraction of such a sericin it is preferable that the extraction be performed using hot water not containing alkali and the like. By the hot water extraction the sericin can be extracted while retaining a relatively high molecular weight. Besides, since the extract does not contain alkali and the like, such operations as fractionation and desalting are not specially needed. After removal of impurities, the extract is concentrated if necessary and thereafter can be used as it is as an aqueous solution of sericin for the production of a porous body which will be described later.

For removing impurities from the sericin-containing extract there may be adopted a known method such as, for example, filtration or centrifugal separation.

Further, the extract thus obtained is subjected to separation and purification if necessary. In this case, how to effect separation and purification is not specially limited. For example, such known methods as salting-out, organic solvent precipitation, gel filtration chromatography, ion exchange chromatography, reverse phase chromatography, reverse osmosis, ultrafiltration, ultracentrifugation, and electrodialysis, may be used each alone or in combination. Further, drying such as freeze drying or spray drying may be performed. By adjusting conditions in these steps there is obtained sericin having an average molecular weight of 30000 to 400000.

The aqueous solution of sericin used in producing the porous body of the present invention may be the above extract or a separated and purified product thereof, or may be prepared by dissolving in water a solid sericin obtained by drying. As will be described later, the aqueous solution of sericin gels at a certain temperature or lower insofar as it is prepared while satisfying gelation characteristics, so in order for the aqueous solution of sericin to retain properties as liquid, it is necessary that the aqueous solution of sericin be held at a higher temperature. However, even if it gels, its properties as liquid can be recovered easily by heating. The gelation temperature cannot be specified unconditionally because it differs greatly depending on the molecular weight and concentration of sericin.

The porous body of the present invention is characterized by being a structure obtained by precipitating sericin in a porous form from the above aqueous solution of sericin and having a recovery rate after 50% compression of 10 to 100%. If the recovery rate after 50% compression is less than 10%, the strength of the porous body concerned is low and cannot withstand practical use. Preferably, the recovery rate is in the range of 20 to 100%.

It is preferable that the skeletal structure of the porous body according to the present invention be substantially formed by sericin alone.

An average pore diameter of the porous body according to the present invention is usually in the range of 0.1 to 5000 μm and any of porous bodies falling under this range in average pore diameter is employable as a functional material insofar as it has a practical strength. If the average pore diameter is smaller than 0.1 μm, a satisfactory water permeability is not obtained. If the average pore diameter exceeds 1000 μm, there is a fear that it may become impossible to stably immobilize the functional substance. Preferably, the average pore diameter is 0.1 to 1000 μm, more preferably 1 to 500 μm.

The average pore diameter was calculated by selecting fifty pores at random, then measuring the longest diameter of each pore rectilinearly and calculating a mean value.

The porous body of the present invention may have a porosity in the range of 1 to 99.5% and any of porous bodies falling under this range in porosity is employable as a functional material insofar as it has a practical strength. Preferably, the porosity is in the range of 70 to 99%. If the porosity is less than 70%, a satisfactory water permeability is not obtained. If the porosity exceeds 99%, it is impossible to obtain a practical strength. A more preferred porosity is in the range of 85 to 98%.

The porosity of the porous body as referred to herein indicates a porosity obtained by immersing the porous body in water, then measuring the weight (A) of the porous body in a state in which water is retained to the maximum extent within the pores and the weight (B) of the porous body after drying at 50° C. for 6 hours, and making calculation in accordance with the following equation:

$$\text{Porosity}(\%) = [(A-B)/A] \times 100$$

The porous body of the present invention is low in its solubility in water and is therefore employable with water retained in the pores. An appropriate amount of water to be retained in the porous body may be set according to the purpose of use.

Next, a description will be given below about how to produce the porous body according to the present invention.

The porous body of the present invention can be produced by precipitating sericin in a porous form from an aqueous solution containing sericin having an average molecular weight of 30000 to 400000. According to a preferred embodiment, the porous product can be produced by gelling the aqueous solution of sericin, then freezing the resulting gels and subsequently melting the frozen gels.

This method is characteristic in that the aqueous solution of sericin is once gelled, followed by freezing and melting. A porous body produced by subjecting the aqueous solution of sericin to freezing and melting without going through the gelation step is very fragile and cannot retain its structure. Controlling the pore diameter and porosity of the porous body obtained by the method in question into the respective preferred ranges described above can be done by controlling the concentration of the aqueous solution of sericin, the amount of air contained in sericin in gelation, the size of air bubbles contained in sericin gels and the cooling rate in freezing.

The gelation of the aqueous solution of sericin is attained by cooling and/or concentrating the aqueous solution of sericin in a vessel suitable for affording a porous body of a desired shape and maintaining the solution at a gelation temperature or lower. In this case, if the concentration of the aqueous solution of sericin is adjusted beforehand to a value of 0.5 to 20% by weight (hereinafter, simply refer to "wt %"), gelation can be effected by merely cooling the aqueous solution of sericin. This is efficient. If the sericin concentration is lower than 0.5 wt %, gelation does not occur even if cooling is made to 0° C., and the aqueous solution of sericin freezes as it is, making it impossible to precipitate the desired porous body. If the sericin concentration exceeds 20 wt %, the operability is poor because gelation takes place at a high temperature and it is difficult to make control into a desired shape. A more preferred sericin concentration is 1 to 10 wt %. The shape to be obtained is not specially limited, but there may be adopted a suitable shape according to the purpose of use, e.g., sheet(-like), columnar, cubic, or spherical shape.

Moreover, since the gelation temperature can be increased by concentrating the aqueous solution of sericin, it is also possible to let the same solution be gelled thereby.

As examples of the method for concentrating the aqueous solution of sericin, mention may be made of the use of an ultrafilter membrane or the use of an evaporator.

The time required for gelation of the aqueous solution of sericin is time for sufficient gelation of the same solution and differs depending on the concentration and amount of the aqueous solution of sericin, the shape and material of the vessel used, and the cooling temperature and cooling method (e.g., whether in air or in a solvent). For example, in the case where an aqueous solution of sericin obtained by hot water extraction is allowed to stand at room temperature (about 25° C.) in a plastic vessel, and cooled and gelled thereby, 0.5 to 1 hour is needed in case of the desired shape being a columnar shape (about 8 cm$^3$) having a diameter of 1 cm and a height of 10 cm is 0.5 to 1 hour, 1 to 2 hours is needed in case of the desired shape being a columnar shape (about 54 cm$^3$) having a diameter of 9 cm and a height of 15 cm, and 0.5 to 1 hour is needed in case of the desired shape being a sheet having a short side of 10 cm, a long side of 100 cm and a height of 1 cm. However, even if the solution is left standing for a longer time, there will arise no special problem.

Then, the sericin gels are cooled to a temperature lower than 0° C. and are frozen thereby. With cooling, water contained in the sericin gels freezes to form crystals of ice and at the same time sericin precipitates in a porous form. The reason why the thus-precipitated porous body has a practical strength is not clear, but is presumed to be because with growth of the ice crystals the sericin protein present within the sericin gels changes in quality and a new linkage is formed between the sericin molecules.

The temperature at which the sericin gels freeze (hereinafter referred to as the "freezing temperature" is not specially limited, but may be any temperature insofar as the temperature causes the sericin gels to freeze. Practically, it is preferable to freeze the sericin gels at a temperature of −80 to −3° C. with use of a freezer. The freezing temperature capable of being attained by a conventional freezer is about −80° C. If the freezing temperature is higher than −3° C., a long time is required for freezing and freezing does not occur in case of the sericin concentration being high. A more preferred freezing temperature is in the range of −80 to −30° C.

In freezing there may be used a known coolant such as, for example, dry ice—methyl alcohol or liquid nitrogen.

The time required for freezing of the sericin gels is not specially limited insofar as water contained in the sericin gels freezes to a satisfactory extent and sericin precipitates. It differs depending on the concentration and volume of the sericin gels, the shape and material of the vessel used, and the cooling temperature and cooling method (e.g., whether in air or in a solvent). For example, in the case where sericin gels obtained by gelation at room temperature (about 25° C.) in a plastic vessel are allowed to stand within a freezer held at −30° C. and are frozen thereby, 0.5 to 2 hours is needed in case of the desired shape being a columnar shape (about 8 cm$^3$) having a diameter of 1 cm and a height of 10 cm, 3 to 6 hours is needed in case of the desired shape being a columnar shape (about 954 cm$^3$) having a diameter of 9 cm and a height of 15 cm, and 0.5 to 2 hours is needed in case of the desired shape being a sheet(-like) shape (1000 cm$^3$) having a short side of 10 cm, a long side of 100 cm and a height of 1 cm. Even if the sericin gels are left standing for a longer time, there will arise no special problem.

As described previously, the pore diameter of the porous body can be adjusted by controlling the cooling rate in freezing. For example, if rapid cooling is performed using liquid nitrogen, it is possible to obtain a porous body of sericin smaller in pore diameter than in the case of slow cooling using a freezer held at −30° C.

Then, the frozen sericin gels (at this stage a porous body constituted by the sericin skeleton is precipitated within the sericin gels in a state of ice crystals being held in pores) are allowed to stand at a temperature of 0° C. or higher and are melted thereby. The temperature at which the gels are to be melted ("melting temperature" hereinafter) is not specially limited. Any temperature will do if the frozen sericin gels melt at that temperature. Preferably, the melting temperature is 0 to 80° C., more preferably 4 to 40° C. If the melting temperature is lower than 0° C., a long time is required for the melting, and melting does not occur if the sericin concentration is low. If the melting temperature exceeds 80° C., the porous body dissolves in water. The time required for melting the frozen sericin gels is set to a time in which the ice present in the frozen sericin gels melts to a satisfactory extent. It differs depending on the concentration and volume of the sericin gels, the shape and material of the vessel used, and the melting temperature and melting method (e.g., whether in air or in a solvent). For example, in the case where sericin gels frozen at −30° C. are to be melted by allowing the gels to stand at room temperature (about 25° C.) within a plastic vessel, 1 to 2 hours is needed in case of the desired shape of a porous body being a columnar shape (about 8 $cm^3$) having a diameter of 1 cm and a height of 10 cm, 6 to 12 hours is needed in case of the desired shape being a columnar shape (about 954 $cm^3$) having a diameter of 9 cm and a height of 15 cm, and 1 to 2 hours is needed in the case of a sheet(-like) shape (1000 $cm^3$) having a short side of 10 cm, a long side of 100 cm and a height of 1 cm. However, even if the sericin gels are left standing for a longer time, there will arise no special problem.

In this way it is possible to obtain a porous body with a large amount of water retained in pores. The water present in the pores can be removed by compressing the pore body or by bringing a towel or a water absorbing substance with the porous body. As described above, the amount of water to be retained in the porous body may be set suitably according to the purpose of use. By heating and dissolving the porous body after suitably adjusting the amount of water to be retained in the porous body it is possible to prepare a concentrated aqueous solution of sericin.

On drying or with a decrease in the amount of retained water, the porous body contracts and lowers in its porosity; besides, it tends to becomes less flexible. The contraction of the porous body caused by drying can be prevented by substituting the water contained in the porous body with an alcohol such as, for example, methanol or ethanol. This treatment is preferred in the case where a porous body high in porosity and small in the amount of retained solvent is to be obtained.

The recovery rate after 50% compression of the porous body thus obtained is usually in the range of 10 to 100% and thus satisfies the foregoing condition.

The porous body of the present invention is flexible, but nevertheless is rich in elasticity, and although it is deformed temporarily when grasped firmly, it can revert to its original shape upon release from pressure. Further, its solubility in water is low. Thus, the porous body of the present invention has a strength able to withstand practical use as a functional material.

As noted earlier, the pore diameter and porosity of the porous body can be adjusted by controlling the concentration of the aqueous solution of sericin, the amount of air contained in sericin in gelation, the size of air bubbles contained in sericin gels and the cooling rate in freezing. But it is also possible make the adjustment by compression or contraction after precipitation of the porous body.

In the porous body of the present invention, various functional substances can be immobilized in a physically stabilized state. As examples of functional substances, mention may be made of living body-derived substances such as polypeptides, e.g., antibodies and enzymes, nucleic acid, polysaccharides, and vitamins. These substances may be in a combined state of two or more.

The porous body of the present invention can suppress deactivation of the functional substance concerned which can occur due to stress such as freezing. Thus, it is effective also in case of immobilizing, for example, an enzyme high in freeze-sensitivity.

Such a functional substance can be immobilized uniformly to the porous body by dissolving or dispersing it into an aqueous solution of sericin when preparing the same solution.

The porous body of the present invention may be a composite with such a structure as a fiber or a resin molding. This composite can be produced easily by immersing the structure in an aqueous solution of sericin and allowing sericin to precipitate in this state. It goes without saying that the functional substance may be immobilized to the composite.

EXAMPLES

The present invention will be described in more detail below by way of working examples, but the invention is not limited to the following examples.

Example 1

100 g of domestic silkworm cocoons after removal of pupae were immersed in 100 g of ion-exchange water and were heated at 105° C. for 30 minutes with use of an autoclave. The resultant extract was filtered using a glass filter (ADVANTEC GA-100, a product of Toyo Roshi Co., Ltd.) to remove impurities, affording about 1 wt % of an aqueous solution of sericin.

An average molecular weight of sericin obtained was measured by SDS-PAGE and was found to be about 100000.

1.0 ml of the aqueous solution of sericin prepared above was poured into a microtube (1.5 ml) and was left standing at room temperature (about 25° C.) for 1 hour, allowing gelation of the solution to take place, followed by standing at −30° C. for 15 hours to freeze sericin gels. Next, the sericin gels were allowed to stand at room temperature for 6 hours and were melted thereby. The melt was withdrawn from the microtube, affording a porous body having a porosity of about 97% and with water retained in pores.

The porous body was immersed in ethanol to substitute water with ethanol and was then dried. As a result of observation through an electron microscope it turned out that pores of 10 to 400 μm (average pore diameter: 110 μm) were formed. FIG. 1 shows an electron micrograph.

The porous body with water retained in pores was evaluated for its solubility (temperature stability and pH stability), the results of which are shown in Tables 1 and 2. The evaluation was made by the following methods.

Solubility (Temperature Stability)

The porous body was immersed in 0.5 ml of a 50 mM phosphoric acid buffer solution with a pH value of 7.0 and was left standing at each of temperatures of 4° C., 25° C., 37° C., 50° C., 60° C. and 80° C. for 1 hour. The porous body-immersed solution were each filtered using a 0.45 μm syringe filter (a product of Asahi Techno Glass Corp.) to remove impurities and was then determined for protein concentration by the BCA method (Micro BCA™ Protein Assay Reagent, a product of PIERCE Co., Ltd.). The solubility of the porous body was determined on the assumption that the protein concentration in a completely dissolved state of the porous body by heating corresponded to 100% solubility.

Solubility (pH Stability)

The porous body was immersed in each of 0.5 ml of a 50 mM hydrochloric acid buffer solution with a pH value of 4.5 and 0.5 ml of 50 mM phosphoric acid buffer solutions with pH values of 6.0, 7.0 and 8.0, followed by standing at 25° C.

for 1 hour. The porous body-immersed solutions were each filtered using a 0.45 μm syringe filter (a product of Asahi Techno Glass Corp.) to remove impurities and were then determined for protein concentration by the BCA method (Micro BCA™ Protein Assay Reagent, a product of PIERCE Co., Ltd.). The solubility of the porous body was determined on the assumption that the protein concentration in a completely dissolved state of the porous body by heating corresponded to 100% solubility.

Example 2

25 ml of the aqueous solution of sericin with a concentration of about 1 wt % prepared in Example 1 was poured into a plastic tube (50 ml) having a conical bottom, followed by the same procedure as in Example 1, to afford a porous body with water retained in pores. The porous body of sericin thus obtained was then squeezed to decrease the content of water and was dissolved again by heating. Thereafter, ion-exchange water was added to adjust the amount of the solution to 10 ml, affording an aqueous solution having a sericin concentration of about 2.5 wt %.

The procedure of Example 1 was repeated except that the aqueous solution of sericin with a concentration of about 2.5 wt % prepared above was used, affording a porous body having a porosity of about 95% and with water retained in pores.

The porous body thus obtained was evaluation for solubility (temperature stability and pH stability) in the same way in Example 1, the results of which are shown in Tables 1 and 2.

TABLE 1

| | Solubility (%) | |
|---|---|---|
| Temperature (° C.) | Example 1 | Example 2 |
| 4 | ≦1 | ≦1 |
| 25 | ≦1 | ≦1 |
| 37 | 5.0 | ≦1 |
| 50 | 24.4 | 4.7 |
| 60 | 31.2 | 5.9 |
| 80 | 62.7 | 41.9 |

TABLE 2

| | Solubility (%) | |
|---|---|---|
| pH | Example 1 | Example 2 |
| 1.7 | ≦1 | ≦1 |
| 4.5 | ≦1 | ≦1 |
| 6.0 | ≦1 | ≦1 |
| 7.0 | ≦1 | ≦1 |
| 8.0 | ≦1 | ≦1 |

Example 3

640 ml of the aqueous solution of sericin with a concentration of about 1 wt % prepared in Example 1 was poured into a beaker (1 liter), followed by the same procedure as in Example 1, to afford a porous body with water retained in pores. The porous body of sericin thus obtained was then squeezed to decrease the content of water and was dissolved again by heating. Thereafter, ion-exchange water was added to adjust the amount of the solution to 80 ml, affording an aqueous solution having a sericin concentration of about 8 wt %. Further, this aqueous solution was diluted to afford 40 ml of an aqueous solution having a sericin concentration of about 2 wt % and 40 ml of an aqueous solution having a sericin concentration of about 6 wt %.

25 ml of each of the aqueous solutions of sericin with concentrations of about 2 wt %, about 6 wt % and about 8 wt % prepared above was poured into a plastic tube (50 ml) having a conical bottom, followed by the same procedure as in Example 1, to afford porous bodies with water retained in pores. The porous bodies were found to have porosities of about 96%, about 89%, and about 86%, respectively.

The porous bodies were then immersed in ethanol and the porous bodies with ethanol thus retained in pores were evaluated for recovery after 50% compression, the results of which are shown in Table 3. The evaluation was made by the following methods.

Recovery After 50% Compression

A columnar porous body having a radius of 2.4 cm and a height of 3.0 cm was sampled and compressed to a height ratio of 50% at a compression rate of 30 mm/min with use of a universal tester (autograph EZTest/CE, a product of Shimazu Co., Ltd.), followed by removal of pressure at the same rate. Subsequently, the height (H) of the porous body was measured and the recovery rate was determined in accordance with the following equation:

Recovery rate(%)=[($H$−1.5)/1.5]×100

TABLE 3

| Sericin Concentration (%) | Compression Recovery Rate (%) |
|---|---|
| 2 | 25 |
| 6 | 50 |
| 8 | 75 |

Comparative Example 1

1 kg domestic silkworm cocoons after removal of pupae were immersed in 50 liters of an aqueous solution of sodium carbonate (pH 11 to 12) with a concentration of 0.2 wt % and were heated at 95° C. for 2 hours to hydrolyze and extract sericin (the sericin hydrolyzate may be merely called sericin as the case may be). The resultant extract was filtered by means of a filter having an average hole diameter of 0.2 μm to remove impurities. Thereafter, the filtrate was desalted using a reverse osmosis membrane to afford a colorless, transparent, aqueous solution of sericin with a concentration of about 0.2 wt %. Then, this solution was concentrated to a sericin concentration of about 2 wt % with use of an evaporator, followed by freeze-drying, to afford 100 g of a powdered sericin hydrolyzate. An average molecular weight of the sericin hydrolyzate was determined by SDS-PAGE and was found to be about 20000.

The sericin powder was dissolved in ion-exchange water to afford a 20 wt % aqueous solution of sericin. 1.0 ml of the aqueous solution of sericin was poured into a microtube (1.5 ml) and was left standing at room temperature (about 25° C.) for 1 hour. But gelation of the aqueous solution of sericin did not occur. Thereafter, the aqueous solution of sericin was allowed to stand at −30° C. for 15 hours and was frozen thereby. Then, the frozen mass was allowed to stand at room temperature for 6 hours and was melted thereby. However, precipitation of the desired porous body was not recognized.

Example 4

Tyrosinase was immobilized to a porous body. More particularly, 100 units of a mushroom-derived tyrosinase powder (manufactured by Sigma Co., Ltd.) was mixed into 1.0 ml of the aqueous solution of sericin with a concentration of about 2.5 wt % prepared in Example 2 and the resultant mixed aqueous solution was poured into an empty column (2.5 ml), followed by standing in ice water for 1 hour, causing gelation of the mixed aqueous solution to take place. Thereafter, the gels thus formed were allowed to stand at −30° C. for 15 hours to freeze the gels, followed by melting of the frozen gels at 4° C. for 6 hours to afford a column packed with a tyrosinase-immobilized porous body. The column thus obtained was washed with 10 ml of a 50 mM phosphoric acid buffer solution with a pH value of 7.0 to remove unimmobilized tyrosinase. The thus-washed column was then subjected to the following evaluation tests 1 and 2.

Evaluation Test 1

1.0 ml of a 0.1 wt % aqueous solution of D-tyrosine as a substrate was added into the column from an upper portion of the column and was allowed to react at room temperature (about 25° C.) for 1 hour. Thereafter, pressure was applied from the upper portion of the column and the reaction solution was recovered from a lower portion of the column.

As a control, a solution of 100 units of tyrosinase in 1.0 ml of a 50 mM phosphoric acid solution with a pH value of 7.0 was added into 1.0 ml of a 0.1 wt % aqueous solution of D-tyrosine and was allowed to react at room temperature for 1 hour.

The activity of tyrosinase was determined by measuring the amount of the resultant dopaquinone in terms of absorbance at 475 nm. The results obtained are shown in Table 4 below.

TABLE 4

|  | Absorbance | Relative ratio (%) |
| --- | --- | --- |
| Enzyme immobilized to the porous body | 0.161 | 87 |
| Control | 0.186 | 100 |

In the porous body of sericin according to the present invention, as is seen from Table 4, tyrosinase could be immobilized to the porous body without deactivation thereof.

Evaluation Test 2

100 ml of a 0.1 wt % aqueous solution of D-tyrosine as a substrate was permeated to a column from an upper portion of the column at a flow rate of 1.0 ml/min and the reaction solution was withdrawn 5 ml each time from a lower portion of the column. An enzyme reaction was performed at room temperature (about 25° C.).

5 ml each of the reaction solutions recovered in 5 ml from the start of permeation, 45 to 50 ml, and 95 to 100 ml, was determined for tyrosinase activity in the same way as in Evaluation Test 1, then a percent activity retention was determined, assuming that the activity just after the start of permeation was 100%. The results obtained are shown in Table 5 below.

TABLE 5

| Permeating Solution (ml) | Absorbance | Percent Activity Retention (%) |
| --- | --- | --- |
| 5 from the start of permeation | 0.121 | 100 |
| 45~50 | 0.127 | 105 |
| 95~100 | 0.111 | 92 |

As is seen from Table 5, also after permeation of 100 ml of the substrate solution, the porous body of the present invention had tyrosinase immobilized thereto while retaining 90% or more activity.

BRIEF DESCRIPTION OF THE DRAWING

FIG. 1 is an electron micrograph of a porous body according to the present invention.

The invention claimed is:

1. A porous body having a recovery rate of 10 to 100% after 50% compression consisting of a porous skeleton formed of a material consisting of sericin having an average molecular weight of 30000 to 400000.

2. The porous body of claim 1 having an average pore diameter of 0.1 to 5000 μm.

3. The porous body of claim 1 having a porosity of 70 to 99%.

4. The porous body of claim 2 having a porosity of 70 to 99%.

5. The porous body of claim 1 wherein said skeleton is obtained by gelling an aqueous solution of a material consisting of sericin with an average molecular weight of 30,000 to 400,000, thereafter freezing the resulting gel and then allowing the frozen gel to thaw to obtain said porous body.

6. A porous body having a recovery rate of 10% to 100% after 50% compression consisting of:
   a porous skeleton formed of a material consisting of sericin having an average molecular weight of 30000 to 400000, and,
   a functional substance immobilized in the skeleton.

7. The porous body of claim 6 wherein the functional substance is a living body-derived substance.

8. A porous body obtained by gelling an aqueous solution containing sericin with an average molecular weight of 30,000 to 400,000, thereafter freezing the resulting gel and then allowing the frozen gel to thaw, wherein said porous body has a recovery rate of 10% to 100% after 50% compression.

* * * * *